United States Patent
Stonecipher

(10) Patent No.: US 9,882,182 B2
(45) Date of Patent: Jan. 30, 2018

(54) BATTERY HOUSING

(71) Applicant: Caterpillar Inc., Peoria, IL (US)

(72) Inventor: Kenneth Stonecipher, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 214 days.

(21) Appl. No.: 14/872,604

(22) Filed: Oct. 1, 2015

(65) Prior Publication Data

US 2017/0098801 A1    Apr. 6, 2017

(51) Int. Cl.
*H01M 2/02* (2006.01)
*H01M 2/04* (2006.01)
*C12N 13/00* (2006.01)

(52) U.S. Cl.
CPC ............ *H01M 2/029* (2013.01); *C12N 13/00* (2013.01); *H01M 2/0295* (2013.01)

(58) Field of Classification Search
CPC ... H01M 2/029; H01M 2/0282; H01M 2/0295
See application file for complete search history.

(56) References Cited

U.S. PATENT DOCUMENTS

| | | | |
|---|---|---|---|
| 6,040,080 A | 3/2000 | Minami et al. | |
| 8,124,263 B2 | 2/2012 | Hermann | |
| 8,137,833 B1 | 3/2012 | Hermann | |
| 8,173,289 B2 | 5/2012 | Mitsuda et al. | |
| 8,763,742 B1 | 7/2014 | Borumand et al. | |
| 8,835,033 B2 | 9/2014 | Choi et al. | |
| 2008/0145577 A1* | 6/2008 | Bayer | A01G 1/046 428/35.6 |
| 2011/0269209 A1 | 11/2011 | Rocco et al. | |
| 2013/0052518 A1 | 2/2013 | Harris et al. | |

FOREIGN PATENT DOCUMENTS

| | | |
|---|---|---|
| DE | 102011090003 | 7/2013 |
| EP | 1164646 | 7/2008 |
| JP | 2008034556 | 2/2008 |
| KR | 20120111686 | 10/2012 |
| WO | 2013098121 | 7/2013 |

\* cited by examiner

*Primary Examiner* — Jonathan Jelsma
(74) *Attorney, Agent, or Firm* — Miller, Matthias & Hull

(57) ABSTRACT

A cell housing is disclosed. The cell housing may include a case extending between a first side, a second side, an open top end and an integrated bottom end. The cell housing may additionally include a body extending between an inner surface and an outer surface and the body may include a first layer comprising a first three-dimensional network of fibers including α-glucan and chitin, a second layer comprising a second three-dimensional network of fibers including α-glucan and chitin and include a plurality of cellulosic fibers positioned between the first layer and the second layer.

16 Claims, 6 Drawing Sheets

BATTERY HOUSING

TECHNICAL FIELD

This disclosure generally relates to battery housings and, more specifically, relates to corrosion resistant battery housings.

BACKGROUND

Cell housings associated with batteries commonly include a case and a cap. The case commonly includes a body extending between an inner surface and an outer surface, and the inner surface defines an inner space configured to hold a cell, such as a lithium ion cell, including an electrolyte. The cap generally includes a cap-body extending between a top surface and a bottom surface, and the cap assembly is configured to seal against an open end of the casing to thereby enclose the cell.

One cell housing design is described by U.S. Pat. No. 8,137,833 to Hermann (the '833 patent). As seen there, the '833 patent discloses a case including a body extending between an inner surface and an outer surface, and the inner surface defines an inner space configured to hold a cell, such as a lithium ion cell, including an electrolyte. This case is typically comprised of metal that is non-reactive with the cell, including the electrolyte. Furthermore, the '833 patent discloses a cap assembly including a cap-body extending between a top surface and a bottom surface, and the cap assembly is configured to seal against an open end of the casing to thereby enclose the cell. This cap assembly is also comprised of metal that is non-reactive with the cell, including the electrolyte.

Although the metallic materials used to make the case and the cap of the '833 patent may be non-reactive to the cell and electrolyte, these materials may be susceptible to galvanic or electrolytic corrosion with respect to each other under certain conditions. For example, when condensation or water accumulates at an interface between the case and cap, electrolytic and galvanic corrosion may occur. As a result, the particular battery may fail, which in turn may cause other batteries of a battery pack to fail as well. Therefore, a need exists to provide a cell housing that is not only non-reactive to the cell and electrolyte, but that also minimizes the probability that electrolytic and galvanic corrosion may occur.

The present disclosure is directed to overcoming one or more problems set forth above and/or other problems associated with the prior art.

SUMMARY

In accordance with one aspect of the present disclosure, a cell housing is disclosed. The cell housing may include a case extending between a first side, a second side, an open top end and an integrated bottom end. The cell housing may additionally include a body extending between an inner surface and an outer surface and the body may include a first layer comprising a first three-dimensional network of fibers including α-glucan and chitin, a second layer comprising a second three-dimensional network of fibers including α-glucan and chitin and include a plurality of cellulosic fibers positioned between the first layer and the second layer.

In accordance with another aspect of the present disclosure, a battery is disclosed. The battery may include a case extending between a first side, a second side, an open top end and an integrated bottom end. The first side, the second side and the integrated bottom end may further include a body extending between an inner surface and an outer surface, and the inner surface may define an inner space. The body may comprise a first layer comprising a first three-dimensional network of fibers including α-glucan and chitin, a second layer comprising a second three-dimensional network of fibers including α-glucan and chitin and include a plurality of cellulosic fibers positioned between the first layer and the second layer. The battery may further include a cap. The cap may include a cap-body extending between a top surface and a bottom surface. The cap-body may include a third layer comprising a third three-dimensional network of fibers including α-glucan and chitin and a fourth layer comprising a fourth three-dimensional network of fibers including α-glucan and chitin. The battery may additionally include a cell positioned in the inner space.

In accordance with another embodiment of the present disclosure, a method of manufacturing a cell housing is disclosed. The method may include the step of growing mycelium for a period of one to twenty days while exposed to a magnetic field to produce a first layer comprising a first three-dimensional network of fibers, and curing the first layer comprising the first three-dimensional network of fibers at a temperature of at least one hundred and fifty degrees Fahrenheit to terminate growth of the first layer comprising the first three-dimensional network of fibers. Additionally, the method may include the step of growing mycelium for a period of one to twenty days while exposed to a magnetic field to produce a second layer comprising a second three-dimensional network of fibers, and curing the second layer comprising the second three-dimensional network of fibers at a temperature of at least one hundred and fifty degrees Fahrenheit to terminate growth of the second layer comprising the second three-dimensional network of fibers. The method may additionally include the step of positioning a plurality of cellulosic fibers having a length to diameter ratio of at least ten to one between the first layer comprising the first three-dimensional network of fibers and the second layer comprising the second three-dimensional network of fibers to form a first laminate. Furthermore, the method may include the step of placing the first laminate in a first mold, the first mold having the shape of a case, and exposing the first laminate to a vacuum and a pressure to form the case. In an additional step, the method may include the step of growing mycelium for a period of one to twenty days while exposed to a magnetic field to produce a third layer comprising a third three-dimensional network of fibers, and curing the third layer comprising the third three-dimensional network of fibers at a temperature of at least one hundred and fifty degrees Fahrenheit to terminate growth of the third layer comprising the third three-dimensional network of fibers. Moreover, the method may include the step of growing mycelium for a period of one to twenty days while exposed to a magnetic field to produce a fourth layer comprising a fourth three-dimensional network of fibers, and curing the fourth layer comprising the fourth three-dimensional network of fibers at a temperature of at least one hundred and fifty degrees Fahrenheit to terminate growth of the fourth layer comprising the fourth three-dimensional network of fibers. Also, the method may include the step of placing the third layer comprising the third three-dimensional network of fibers in contact with the fourth layer comprising the fourth three-dimensional network of fibers to form a second laminate. Finally, the method may include the step of placing the second laminate in a second mold, the second mold having the shape of a cap, and exposing the first laminate to a vacuum and a pressure to form the cap.

These and other aspects and features of the present disclosure will be more readily understood when read in conjunction with the accompanying drawings.

BRIEF DESCRIPTION

DETAILED DESCRIPTION OF THE DISCLOSURE

Figure 1:
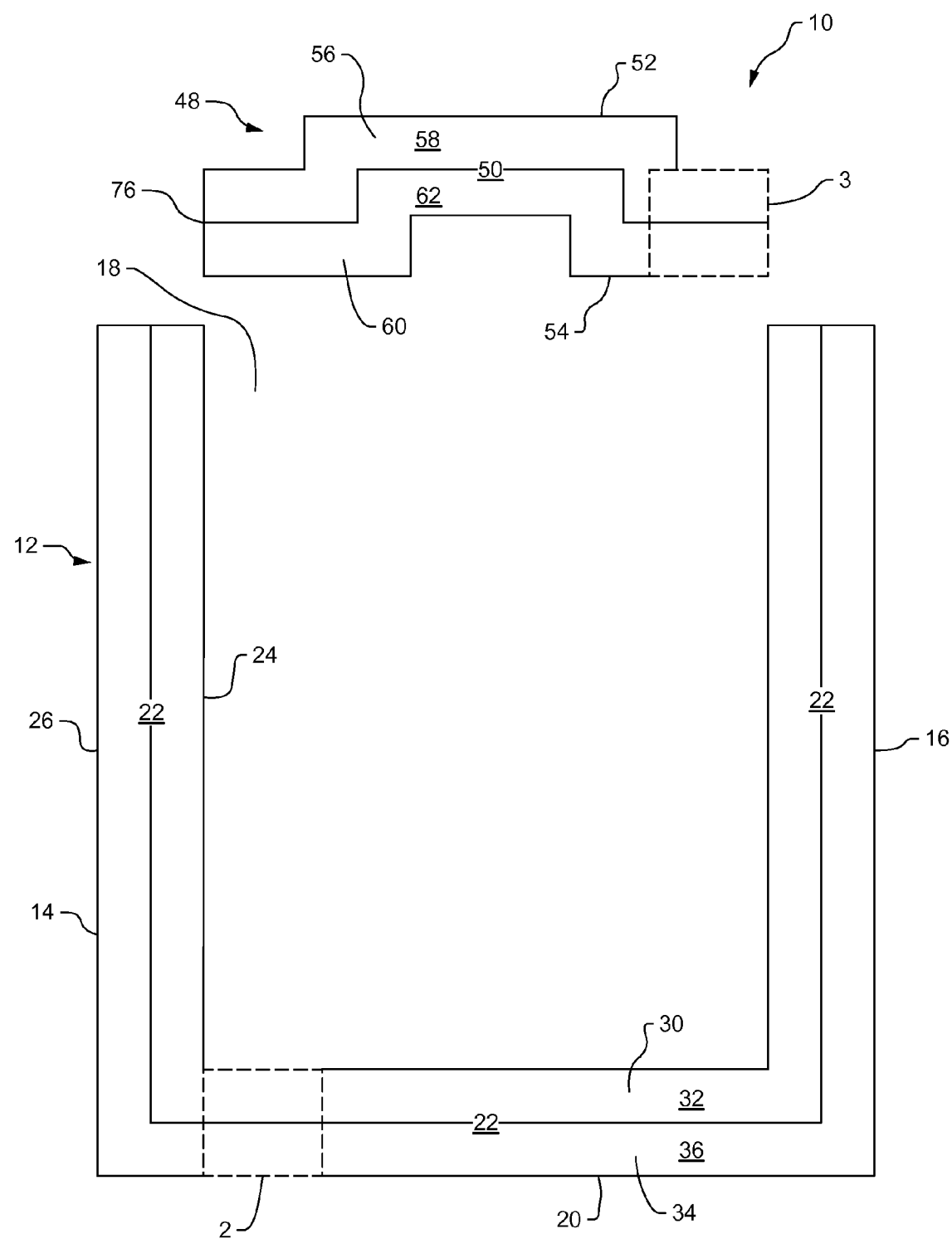
FIG. 1 is a schematic of an exemplary cell housing manufactured in accordance with one aspect of the present disclosure.

Various aspects of the disclosure will now be described with reference to the drawings, wherein like reference numbers refer to like elements, unless specified otherwise. Referring to FIG. 1, a schematic of an exemplary cell housing 10 is illustrated, according to an aspect of the disclosure. The housing 10 may include a case 12 extending between a first side 14, a second side 16, an open top end 18 and an integrated bottom end 20. The first side 14, the second side 16 and the integrated bottom end 20 may further include a body 22 extending between an inner surface 24 and an outer surface 26, and the inner surface 24 may define an inner space 28. Further, the body 22 may comprise a first layer 30 including a first three-dimensional network of fibers 32 including α-glucan and chitin and a second layer 34 including a second three-dimensional network of fibers 36 including α-glucan and chitin. In one embodiment, the first three-dimensional network of fibers 32 is a three-dimensional network of mycelium fibers. In an additional embodiment, the second three-dimensional network of fibers 36 is a three-dimensional network of mycelium fibers.

Figure 2:
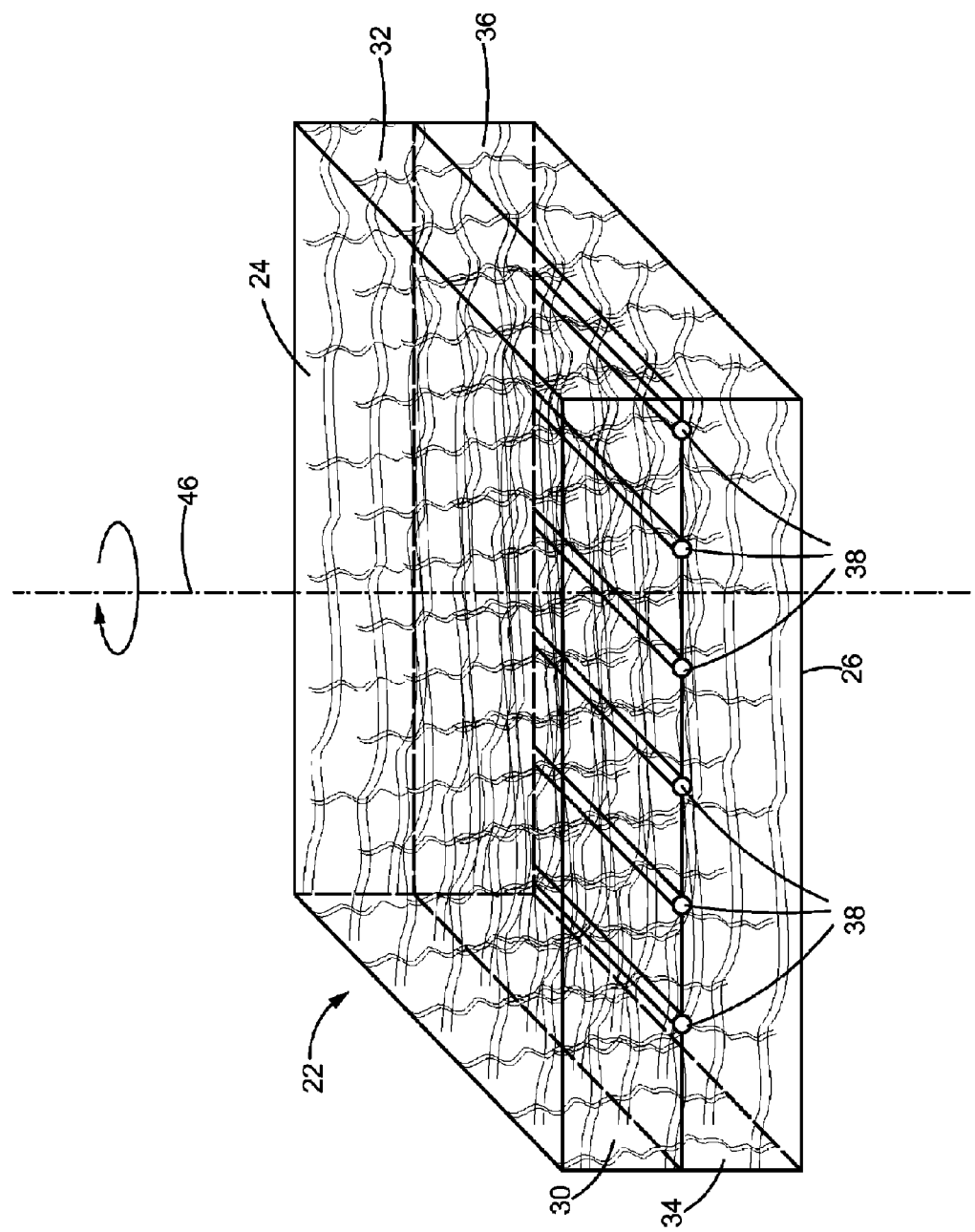
FIG. 2 is an isometric view of portion 2 of FIG. 1 depicting an exemplary body of a case that may be utilized with the cell housing according to FIG. 1.

Turning to FIG. 2, an isometric view of an exemplary body 22 of the case 12 that may be utilized with the housing 10 of FIG. 1 is depicted. As seen there, the body 22 may take the form of a composite. For example, the first three-dimensional network of fibers 32 may be adhered to the second three-dimensional network of fibers 36 by the α-glucan of either the first three-dimensional network of fibers 32 or the second three-dimensional network of fibers 36. Furthermore, the body 22 may be reinforced with a plurality of cellulosic fibers 38 positioned between first layer 30 and the second layer 34. In one embodiment, the plurality of cellulosic fibers 38 has a length to diameter ratio of at least ten to one.

The plurality of cellulosic fibers 38 may be sourced from kenaf, jute, sisal, flax, hemp, coir, switchgrass and mixtures thereof. Furthermore, the plurality of cellulosic fibers 38 may be adhered to the first three-dimensional network of fibers 32 by the α-glucan of the first three-dimensional network of fibers 32, while the plurality of cellulosic fibers 38 may be adhered to the second three-dimensional network of fibers 36 by the α-glucan of the second three-dimensional network of fibers 32. In addition, while FIG. 2 depicts the plurality of cellulosic fibers 38 being oriented in substantially the same direction, it should be understood that other orientations of the plurality of cellulosic fibers 38 is contemplated. For example, the plurality of cellulosic fibers 38 may be oriented in a random distribution. Alternatively, the plurality of cellulosic fibers 38 may be oriented in a cross-hatch pattern.

In an additional embodiment contemplated within the scope of this disclosure, the first layer 30 may have a first average porosity and the second layer 34 may have a second average porosity. In one instance, the first average porosity may be the same as the second average porosity. In another instance, the first average porosity may be different than the second average porosity. In addition, the first layer 30 may define a first plane 40, while the second layer 34 may define a second plane 42. The body 22 may include a first axis of rotation 46 extending through the first plane 40 and the second plane 42, and the second plane 42 may be rotated by about forty five degrees with respect to the first plane 40 about the first axis of rotation 46.

Returning to FIG. 1, the housing 10 may additionally include a cap 48. The cap 48 may include a cap-body 50 extending between top surface 52 and a bottom surface 54. The cap-body 50 may include a third layer 56 including a third three-dimensional network of fibers 58 including α-glucan and chitin and fourth layer 60 including a fourth three-dimensional network of fibers 62 including α-glucan and chitin. In one embodiment, the third three-dimensional network of fibers 58 is a three-dimensional network of mycelium fibers. In an additional embodiment, the fourth three-dimensional network of fibers 62 is a three-dimensional network of mycelium fibers.

Figure 3:
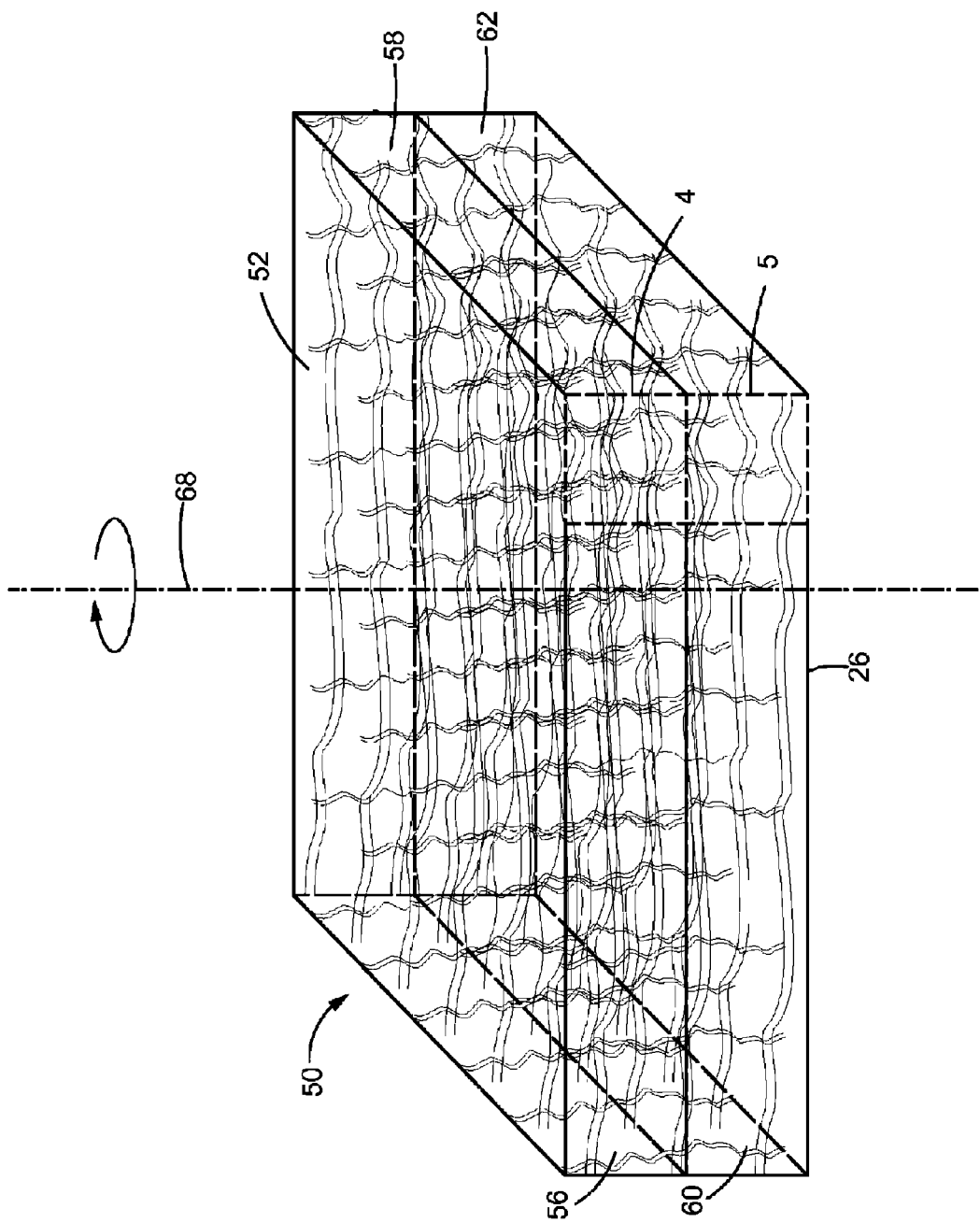
FIG. 3 is an isometric view of portion 3 of FIG. 1 depicting an exemplary cap-body of a cap that may be utilized with the cell housing according to FIG. 1.

Referring to FIG. 3, an isometric portion view of an exemplary cap-body 50 of the cap 48 that may be utilized with the housing 10 of FIG. 1 is depicted. As shown there, the cap-body 50 may take the form of a laminate. For example, the third three-dimensional network of fibers 58 may be adhered to the fourth three-dimensional network of fibers 62 by the α-glucan of either the third three-dimensional network of fibers 58 or the fourth three-dimensional network of fibers 62. In addition, the third layer 56 may having a first average porosity and the fourth layer 60 may have a second average porosity. In one instance, the first average porosity may be the same as the second average porosity. In another instance, the first average porosity may bet different than the second average porosity. Moreover, the third layer 56 may define a third plane 64, while the fourth layer 60 may define a fourth plane 66. The cap-body 50 may also include a second axis of rotation 68 extending through the third plane 64 and the fourth plane 66, and the fourth plane 66 may be rotated by about forty five degrees with respect to the third plane 64 about the second axis of rotation 68.

Figure 4:
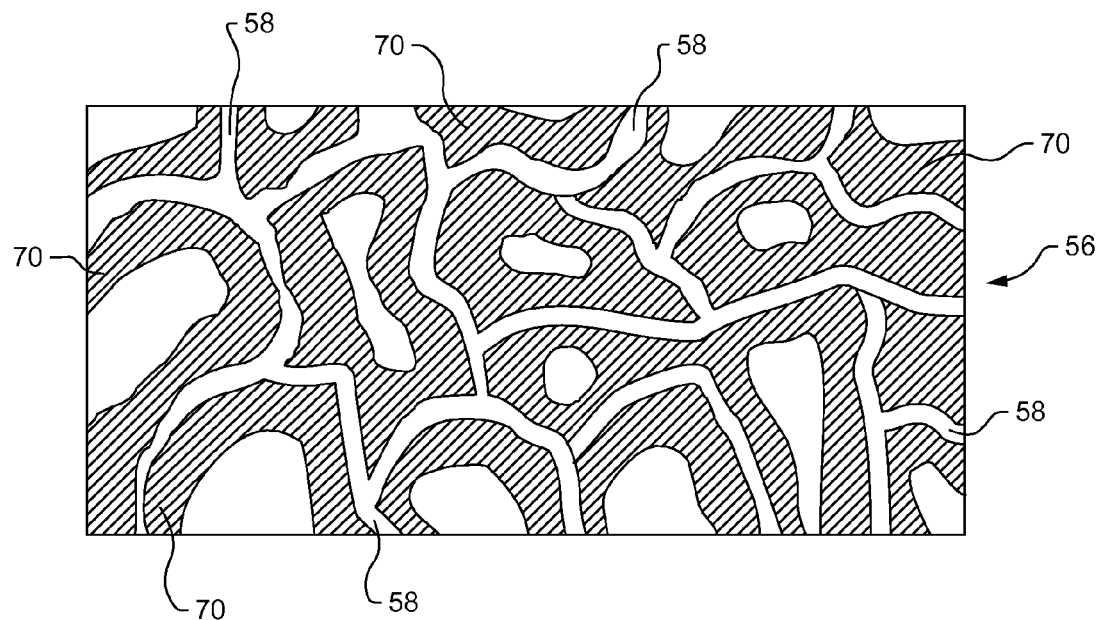
FIG. 4 is a enlarged plan view of portion 4 of FIG. 3 depicting additional features of the exemplary cap-body that may be utilized with the cell housing according to FIG. 1.
Figure 5:
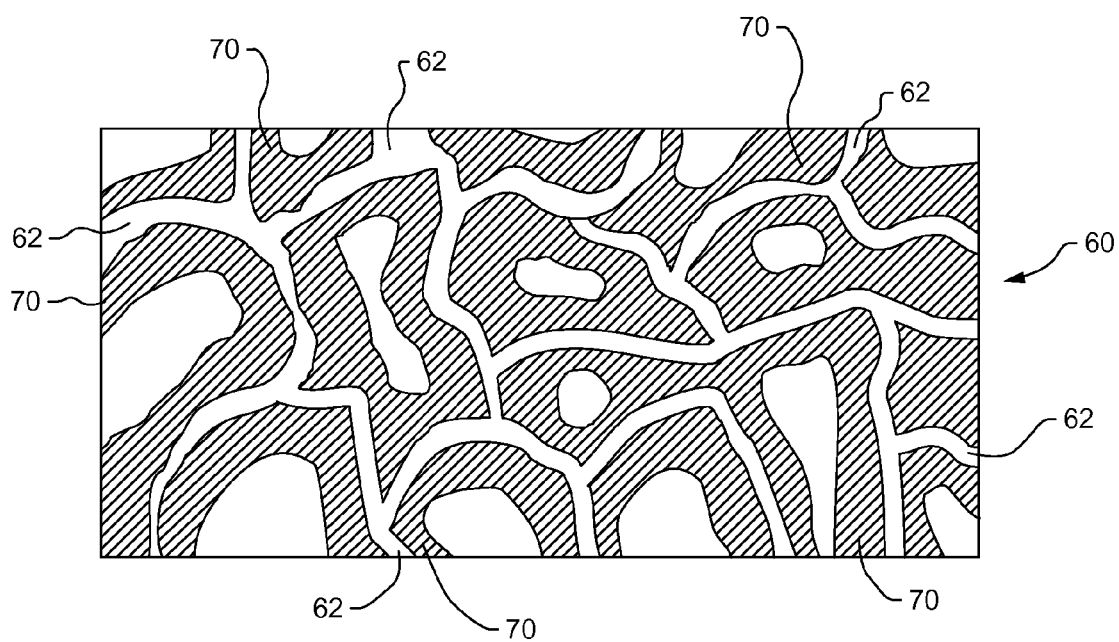
FIG. 5 is a enlarged plan view of portion 5 of FIG. 3 depicting additional features of the exemplary cap-body that may be utilized with the cell housing according to FIG. 1.

Turning to FIGS. 4 and 5, additional features of the third layer 56 and fourth layer 60 of the cap-body 50 that may be utilized with the housing 10 are illustrated. As seen there, the third layer 56 and the fourth layer 60 may be coated with a polymer mixture 70. More specifically, however, the third three-dimensional network of fibers 58 and the fourth three-dimensional network of fibers 62 may be coated with the polymer mixture 70. The polymer mixture 70 may include a polymer and an antioxidant 74. Furthermore, the polymer 72 may be configured to begin thermally degrading at or above a predetermined temperature, while the antioxidant 74 may be included at an amount sufficient to mitigate the polymer 72 from thermally degrading below the predetermined temperature. The polymer 72 contemplated within the scope of this disclosure may be, but is not limited to, polyvinyl benzene, ethylene vinyl acetate, polyethylene, polypropylene, polystyrene, polyethylene terephthalate, polyvinyl chloride, polylactic acid and mixtures thereof. Furthermore, while the following list is only exemplary, antioxidant 74 that may be added to the polymer mixture 70 includes dicarboxylic acids such as oxalic acid, malonic acid, succinic acid, glutaric acid, adipic acid, pimelic acid, suberic acid, azealaic acid, sebacic acid, and the like, $\alpha$-tocopherol, thioesters and mixtures thereof.

Turning back to FIG. 1, the cap 48 may additionally include an outside surface 76. The outside surface 76 may be configured to be in sealing engagement with the inner surface 24 of the case 12. When the outside surface 76 is in sealing engagement with the inner surface 24, the housing 10 may be configured to enclose a cell 78.

Figure 6:
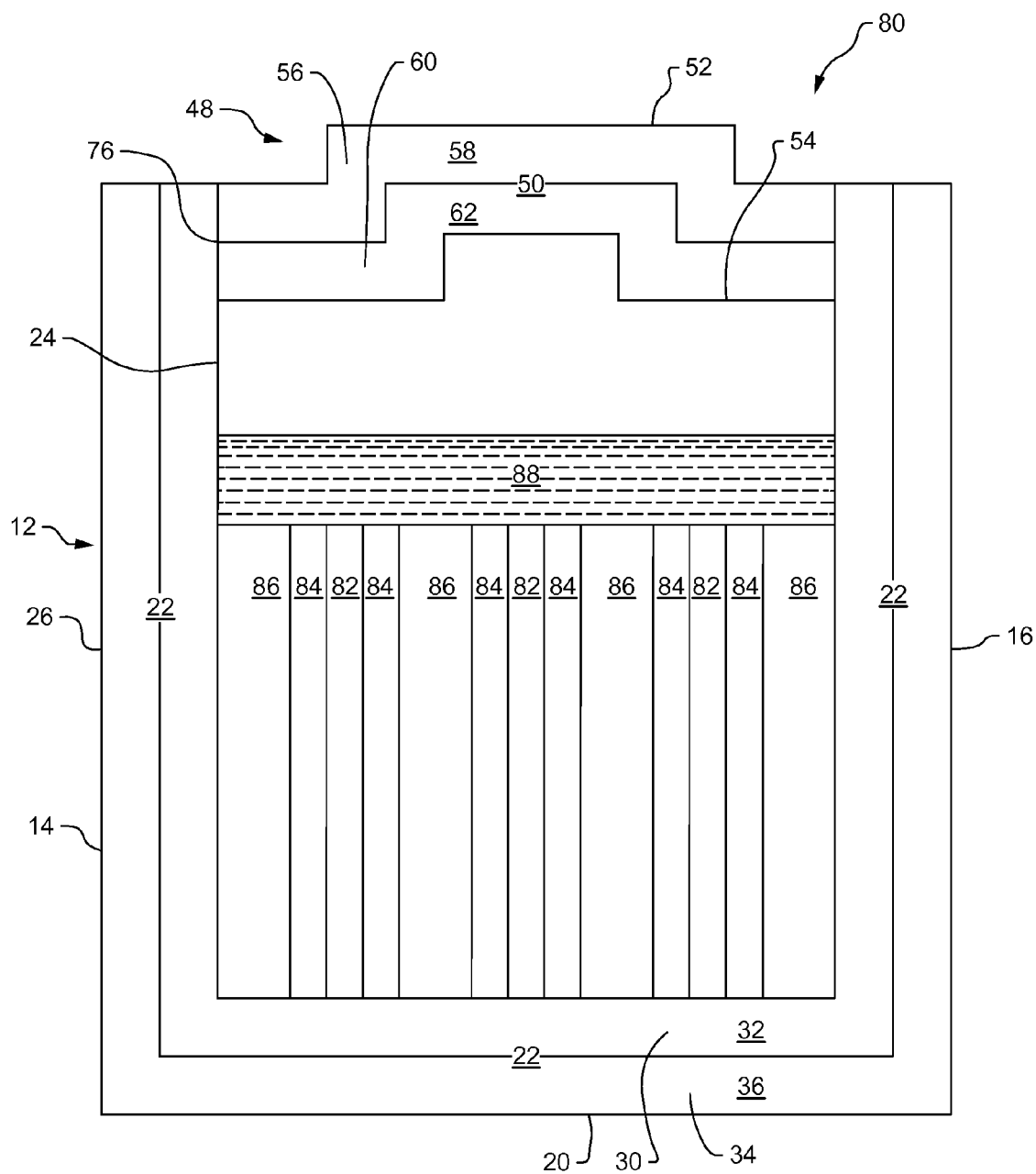
FIG. 6 is a schematic of an exemplary battery utilizing the cell housing according to FIGS. 1-5.

Referring to FIG. 6, an exemplary battery 80 utilizing the housing 10 according to FIGS. 1-5 is depicted, according to another aspect of the present disclosure. As seen there, the battery 80 may include housing 10, and the housing 10 may include a case 12 extending between a first side 14, a second side 16, an open top end 18 and an integrated bottom end 20. The first side 14, the second side 16 and the integrated bottom end 20 may further include a body 22 extending between an inner surface 24 and an outer surface 26, and the inner surface 24 may define an inner space 28. The cell 78 may be positioned in the inner space 28.

Further, the body 22 may comprise a first layer 30 including a first three-dimensional network of fibers 32 including $\alpha$-glucan and chitin and a second layer 34 including a second three-dimensional network of fibers 36 including $\alpha$-glucan and chitin. In one embodiment, the first three-dimensional network of fibers 32 is a three-dimensional network of mycelium fibers. In an additional embodiment, the second three-dimensional network of fibers 36 is a three-dimensional network of mycelium fibers.

Turning to FIG. 2, an isometric view of an exemplary body 22 of the case 12 that may be utilized with the battery 80 of FIG. 5 is depicted. As seen there, the body 22 may take the form of a composite. For example, the first three-dimensional network of fibers 32 may be adhered to the second three-dimensional network of fibers 36 by the $\alpha$-glucan of either the first three-dimensional network of fibers 32 or the second three-dimensional network of fibers 36. Furthermore, the body 22 may be reinforced with a plurality of cellulosic fibers 38 positioned between first layer 30 and the second layer 34. In one embodiment, the plurality of cellulosic fibers 38 has a length to diameter ratio of at least ten to one.

The plurality of cellulosic fibers 38 may be sourced from kenaf, jute, sisal, flax, hemp, coir, switchgrass and mixtures thereof. Furthermore, the plurality of cellulosic fibers 38 may be adhered to the first three-dimensional network of fibers 32 by the $\alpha$-glucan of the first three-dimensional network of fibers 32, while the plurality of cellulosic fibers 38 may be adhered to the second three-dimensional network of fibers 36 by the $\alpha$-glucan of the second three-dimensional network of fibers 32. In addition, while FIG. 2 depicts the plurality of cellulosic fibers 38 being oriented in substantially the same direction, it should be understood that other orientations of the plurality of cellulosic fibers 38 is contemplated. For example, the plurality of cellulosic fibers 38 may be oriented in a random distribution. Alternatively, the plurality of cellulosic fibers 38 may be oriented in a cross-hatch pattern.

In an additional embodiment contemplated within the scope of this disclosure, the first layer 30 may having a first average porosity and the second layer 34 may have a second average porosity. In one instance, the first average porosity may be the same as the second average porosity. In another instance, the first average porosity may bet different than the second average porosity. In addition, the first layer 30 may define a first plane 40, while the second layer 34 may define a second plane 42. The body 22 may include a first axis of rotation 46 extending through the first plane 40 and the second plane 42, and the second plane 42 may be rotated by about forty five degrees with respect to the first plane 40 about the first axis of rotation 46.

Returning to FIG. 6, the battery 80 may additionally include a cap 48. The cap 48 may include a cap-body 50 extending between top surface 52 and a bottom surface 54. The cap-body 50 may include a third layer 56 including a third three-dimensional network of fibers 58 including $\alpha$-glucan and chitin and fourth layer 60 including a fourth three-dimensional network of fibers 62 including $\alpha$-glucan and chitin. In one embodiment, the third three-dimensional network of fibers 58 is a three-dimensional network of mycelium fibers. In an additional embodiment, the fourth three-dimensional network of fibers 62 is a three-dimensional network of mycelium fibers.

Referring to FIG. 3, an isometric portion view of an exemplary cap-body 50 of the cap 48 that may be utilized with the battery 80 of FIG. 6 is depicted. As shown there, the cap-body 50 may take the form of a laminate. For example, the third three-dimensional network of fibers 58 may be adhered to the fourth three-dimensional network of fibers 62 by the $\alpha$-glucan of either the third three-dimensional network of fibers 58 or the fourth three-dimensional network of fibers 62. In addition, the third layer 56 may having a first average porosity and the fourth layer 60 may have a second average porosity. In one instance, the first average porosity may be the same as the second average porosity. In another instance, the first average porosity may bet different than the second average porosity. Moreover, the third layer 56 may define a third plane 64, while the fourth layer 60 may define a fourth plane 66. The cap-body 50 may also include a second axis of rotation 68 extending through the third plane 64 and the fourth plane 66, and the fourth plane 66 may be rotated by about forty five degrees with respect to the third plane 64 about the second axis of rotation 68.

Turning to FIGS. 4 and 5, additional features of the third layer 56 and fourth layer 60 of the cap-body 50 that may be utilized with the battery 80 are illustrated. As seen there, the third layer 56 and the fourth layer 60 may be coated with a polymer mixture 70. More specifically, however, the third three-dimensional network of fibers 58 and the fourth three-dimensional network of fibers 62 may be coated with the polymer mixture 70. The polymer mixture 70 may include a polymer and an antioxidant 74. Furthermore, the polymer 72 may be configured to begin thermally degrading at or above a predetermined temperature, while the antioxidant 74 may be included at an amount sufficient to mitigate the polymer 72 from thermally degrading below the predetermined temperature. The polymer 72 contemplated within the scope of this disclosure may be, but is not limited to, polyvinyl benzene, ethylene vinyl acetate, polyethylene, polypropylene, polystyrene, polyethylene terephthalate, polyvinyl chloride, polylactic acid and mixtures thereof. Furthermore, while the following list is only exemplary, antioxidant 74 that may be added to the polymer mixture 70 includes dicarboxylic acids such as oxalic acid, malonic acid, succinic acid, glutaric acid, adipic acid, pimelic acid, suberic acid, azealaic acid, sebacic acid, and the like, α-tocopherol, thioesters and mixtures thereof.

Turning back to FIG. 6, the cap 48 may additionally include an outside surface 76. The outside surface 76 may be configured to be in sealing engagement with the inner surface 24 of the case 12. When the outside surface 76 is in sealing engagement with the inner surface 24, the housing 10 may be configured to enclose the cell 78.

In addition, the cell 78 may include an anode 82, a cathode 84, a separator 86 and an electrolyte 88. Furthermore, the cell 78 may include a variety of different chemistries including, but not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery 80 type/configuration. Accordingly, the chemistry of the anode 82, the cathode 84, the separator 86 and the electrolyte 88 may differ based upon the type of cell 78 utilized to form battery 80. Furthermore, it should be understood that the case 12 should preferably be impermeable to the electrolyte 88.

INDUSTRIAL APPLICABILITY

In operation, the teachings of the present disclosure can find applicability in many industrial applications, such as, but not limited to, minimizing electrolytic and/or galvanic corrosion of the battery 80. For example, as described above, when condensation or water accumulates at an interface between the case 12 and cap 48, electrolytic and galvanic corrosion may occur. As a result, the particular battery 80 may fail, which in turn may cause other batteries 80 of a battery pack to fail as well. However, since the case 12 and cap 48 of the present disclosure are made of materials resistant to electrolytic and galvanic corrosion (e.g., they do not undergo redox reactions under normal conditions), use of the case 12 and the cap 48 of the present disclosure increases battery 80 longevity, and as a corollary, battery pack life.

Figure 7:
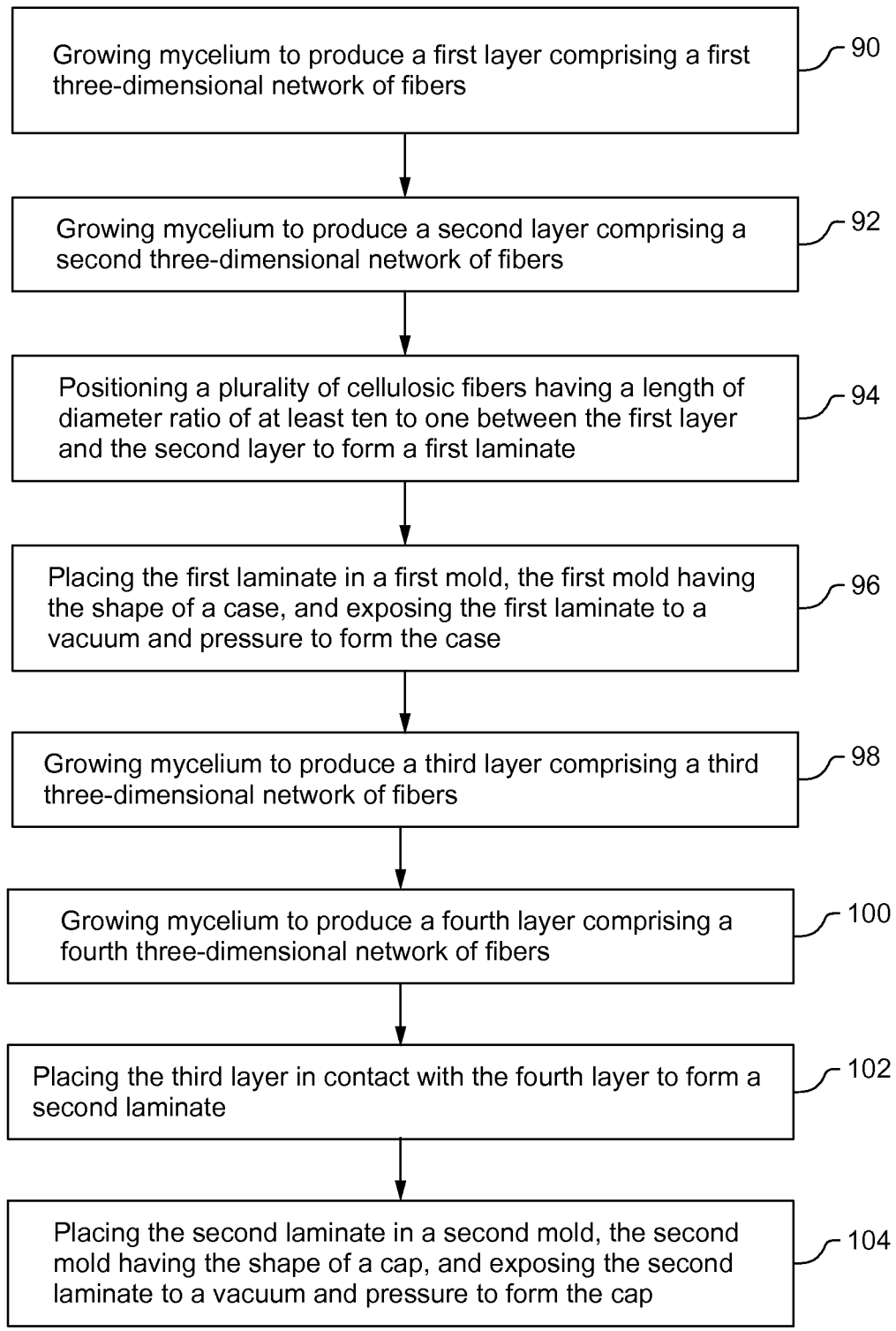
FIG. 7 is a flowchart illustrating exemplary steps of a method of manufacturing for manufacturing the cell housing according to FIG. 1.

Referring now to FIG. 7, an exemplary flowchart is shown depicting a sample sequence of steps that may be followed to manufacture a housing 10 configured to enclose a cell 78 according to the present disclosure. Step 90 of the method may include growing mycelium for a period of one to twenty days while exposed to a magnetic field to produce a first layer 30 comprising a first three-dimensional network of fibers 32, and subsequently curing the first layer 30 comprising the first three-dimensional network of fibers 32 at a temperature of at least one hundred and fifty degrees Fahrenheit to terminate growth of the first layer 30 comprising the first three-dimensional network of fibers 32.

At step 92, the method may include growing mycelium for a period of one to twenty days while exposed to a magnetic field to produce a second layer 34 comprising a second three-dimensional network of fibers 36, and subsequently curing the second layer 34 comprising the second three-dimensional network of fibers 36 at a temperature of at least one hundred and fifty degrees Fahrenheit to terminate growth of the second layer 34 comprising the second three-dimensional network of fibers 36.

In addition, the method may include positioning a plurality of cellulosic fibers 38 having a length to diameter ratio of at least ten to one between the first layer 30 comprising the first three-dimensional network of fibers 32 and the second layer 34 comprising the second three-dimensional network of fibers 36 to form a first laminate at step 94.

Additionally, step 96 of the method may include placing the first laminate in a first mold, the first mold having the shape of a case 12, and exposing the first laminate to a vacuum and a pressure to form the case 12. In one embodiment, the case 12 may extend between a first side 14, a second side 16, an open top end 18 and an integrated bottom end 20, and the first side 14, the second side 16 and the integrated bottom end 20 may further include a body 22 extending between an inner surface 24 and an outer surface 26. The body 22 may include the first layer 30 comprising the first three-dimensional network of fibers 32, the second layer 34 may comprise the second three-dimensional network of fibers 36 and the plurality of cellulosic fibers 38 may have a length to diameter ratio of at least ten to one.

Moving on, step 98 of the method may include growing mycelium for a period of one to twenty days while exposed to a magnetic field to produce a third layer 56 comprising a third three-dimensional network of fibers 58, and subsequently curing the third layer 56 comprising the third three-dimensional network of fibers 58 at a temperature of at least one hundred and fifty degrees Fahrenheit to terminate growth of the third layer 56 comprising the third three-dimensional network of fibers 58.

An additional step 100 of the method may include growing mycelium for a period of one to twenty days while exposed to a magnetic field to produce a fourth layer 60 comprising a fourth three-dimensional network of fibers 62, and curing the fourth layer 60 comprising the fourth three-dimensional network of fibers 62 at a temperature of at least one hundred and fifty degrees Fahrenheit to terminate growth of the fourth layer 60 comprising the fourth three-dimensional network of fibers 62.

Moving on, step 102 of the method may include placing the third layer 56 comprising the third three-dimensional network of fibers 58 in contact with the fourth layer 60 comprising the fourth three-dimensional network of fibers 62 to form a second laminate.

Finally, at step 104, the method may include placing the second laminate in a second mold, the second mold having the shape of a cap 48, and exposing the first laminate to a vacuum and a pressure to form the cap 48. In one embodiment, the cap 48 may include a cap-body 50 extending between a top surface 52 and a bottom surface 54, and the cap-body 50 may include the third layer 56 comprising the third three-dimensional network of fibers 58 and the fourth layer 60 comprising the fourth three-dimensional network of fibers 62. In an additional step, the cap 48 may be coated with a polymer mixture 70, the polymer mixture 70 including a polymer 72 and an antioxidant 74, the polymer 72 configured to begin thermally degrading at or above a predetermined temperature and the antioxidant 74 being included at an amount sufficient to mitigate the polymer 72 from thermally degrading below the predetermined temperature.

The above description is meant to be representative only, and thus modifications may be made to the embodiments described herein without departing from the scope of the disclosure. Thus, these modifications fall within the scope of present disclosure and are intended to fall within the appended claims.

What is claimed is:

1. A cell housing, comprising:
   a case extending between a first side, a second side, an open top end and an integrated bottom end; and a body extending between an inner surface and an outer surface, the body comprising a first layer comprising a first three-dimensional network of fibers including α-glucan and chitin, a second layer comprising a second three-dimensional network of fibers including α-glucan and chitin and a plurality of cellulosic fibers having a length to diameter ratio of at least ten to one positioned between the first layer and the second layer.

2. The cell housing according to claim 1, further including a cap, the cap including a cap-body extending between a top surface and a bottom surface, the cap-body including a third layer comprising a third three-dimensional network of fibers including α-glucan and chitin and a fourth layer comprising a fourth three-dimensional network of fibers including α-glucan and chitin.

3. The cell housing according to claim 2, the first three-dimensional network of fibers being a three-dimensional network of mycelium fibers, the second three-dimensional network of fibers being a three-dimensional network of mycelium fibers, the third three-dimensional network of fibers being a three-dimensional network of mycelium fibers and the fourth three-dimensional network of fibers being a three-dimensional network of mycelium fibers.

4. The cell housing according to claim 1, the first three-dimensional network of fibers being adhered to the second three-dimensional network of fibers by the α-glucan of the first three-dimensional network of fibers or the second three-dimensional network of fibers.

5. The cell housing according to claim 1, the plurality of cellulosic fibers being adhered to the first three-dimensional network of fibers by the α-glucan of the first three-dimensional network of fibers and the plurality of cellulosic fibers being adhered to the second three-dimensional network of fibers by the α-glucan of the second three-dimensional network of fibers.

6. The cell housing according to claim 1, the first layer defining a first plane, the second layer defining a second plane, the body further including a first axis of rotation extending through the first plane and the second plane, the second plane being rotated by about forty five degrees with respect to the first plane about the first axis of rotation.

7. The cell housing according to claim 1, the first layer having a first average porosity, the second layer having a second average porosity.

8. The cell housing according to claim 1, the plurality of cellulosic fibers being oriented in substantially the same direction.

9. The cell housing according to claim 2, the third layer and the fourth layer being coated with a polymer mixture, the polymer mixture including a polymer and an antioxidant, the polymer configured to begin thermally degrading at or above a predetermined temperature, the antioxidant being included at an amount sufficient to mitigate the polymer from thermally degrading below the predetermined temperature.

10. The cell housing according to claim 2, the third layer defining a third plane, the fourth layer defining a fourth plane, the cap-body further including a second axis of rotation extending through the third plane and the fourth plane, the fourth plane being rotated by about forty five degrees with respect to the third plane about the second axis of rotation.

11. A battery, comprising:
a case extending between a first side, a second side, an open top end and an integrated bottom end;
a body extending between an inner surface and an outer surface, the inner surface defining an inner space, the body comprising a first layer comprising a first three-dimensional network of fibers including α-glucan and chitin, a second layer comprising a second three-dimensional network of fibers including α-glucan and chitin and a plurality of cellulosic fibers having a length to diameter ratio of at least ten to one positioned between the first layer and the second layer;
a cap including a cap-body extending between a top surface and a bottom surface, the cap-body including a third layer comprising a third three-dimensional network of fibers including α-glucan and chitin and a fourth layer comprising a fourth three-dimensional network of fibers including α-glucan and chitin; and
a cell positioned in the inner space.

12. The battery according to claim 11, the first three-dimensional network of fibers being a three-dimensional network of mycelium fibers, the second three-dimensional network of fibers being a three-dimensional network of mycelium fibers, the third three-dimensional network of fibers being a three-dimensional network of mycelium fibers and the fourth three-dimensional network of fibers being a three-dimensional network of mycelium fibers.

13. The battery according to claim 11, the first three-dimensional network of fibers being adhered to the second three-dimensional network of fibers by the α-glucan of the first three-dimensional network of fibers or the second three-dimensional network of fibers, the plurality of cellulosic fibers being adhered to the first three-dimensional network of fibers by the α-glucan of the first three-dimensional network of fibers and the plurality of cellulosic fibers being adhered to the second three-dimensional network of fibers by the α-glucan of the second three-dimensional network of fibers.

14. The battery according to claim 11, the plurality of cellulosic fibers being oriented in substantially the same direction.

15. The battery according to claim 11, the third layer and the fourth layer being coated with a polymer mixture, the polymer mixture including a polymer and an antioxidant, the polymer configured to begin thermally degrading at or above a predetermined temperature, the antioxidant being included at an amount sufficient to mitigate the polymer from thermally degrading below the predetermined temperature.

16. The battery according to claim 11, the cell including an anode, a cathode, a separator and an electrolyte, the case being impermeable to the electrolyte.

* * * * *